United States Patent [19]
Tenhoff

[11] Patent Number: 5,724,978
[45] Date of Patent: Mar. 10, 1998

[54] ENHANCED ACCURACY OF THREE-DIMENSIONAL INTRALUMINAL ULTRASOUND (ILUS) IMAGE RECONSTRUCTION

[75] Inventor: Harm Tenhoff, Mountain View, Calif.

[73] Assignee: Cardiovascular Imaging Systems, Inc., Sunnyvale, Calif.

[21] Appl. No.: 717,153

[22] Filed: Sep. 20, 1996

[51] Int. Cl.⁶ .................................................. A61B 8/12
[52] U.S. Cl. ........................................ 128/662.06; 128/916
[58] Field of Search ............................ 128/662.06, 916, 128/661.01, 660.08, 660.09, 660.03

[56] References Cited

U.S. PATENT DOCUMENTS 4,697,595  10/1987  Breyer et al. ........................ 128/660
4,821,731  4/1989  Martinelli et al. ................. 128/662.06

(List continued on next page.)

FOREIGN PATENT DOCUMENTS

WO 95/09562  4/1995  WIPO.
WO 96/05768  2/1996  WIPO.

OTHER PUBLICATIONS

"Image Segmentation and 3D Reconstruction of Intravascular Ultrasound Images", *Acoustical Imaging*, Wei et al., Vol. 20, pp. 489–496.

"ANGUS: A New Approach to Three–Dimensional Reconstruction of Coronary Vessels by Combined Use of Angiography and Intravascular Ultrasound", *Computer in Cardiology* 1995, Laban et al.., pp. 325–328 (Sep. 10–13, 1995).

"Three–Dimensional Geometry and Orientation of Coronary Lumen and Plaque, Reconstruction from Angiography and ICUS (ANGUS)", *The Thoraxcentre Journal*, Slager et al., Vol. 7/3 (1995).

"ANGUS: A New Approach to Three–dimensional Reconstruction of Geometry and Orientation of Coronary Lumen and Plaque by Combined Use of Coronary Angiography and IVUS", Slager et al., *Journal of the American College of Cardiology*, Program and Abstracts of Original Contributions, 734–736 (Feb. 1995).

(List continued on next page.)

*Primary Examiner*—Francis Jaworski
*Attorney, Agent, or Firm*—Lyon & Lyon LPP

[57] ABSTRACT

A method for imaging an organ or internal structure within a body to obtain three-dimensional reconstruction of the organ or internal structure. The method includes steps of providing an intraluminal ultrasound imaging system capable of obtaining echographic images of the surrounding of a catheter imaging tip located inside the body of a patient, and a catheter tracking system comprising at least one ultrasound transducer mounted adjacent the imaging tip of an intraluminal ultrasound catheter for insertion into a patient, a plurality of transducers located away from said intraluminal ultrasound catheter so as to form a reference frame, and circuitry for calculating positions of the plurality of frame transducers relative to each other and positions of said catheter tip transducers relative to said plurality of frame transducers. The intraluminal ultrasound catheter imaging tip is positioned within a region of interest inside the body of the patient and a plurality of echographic images are obtained during deliberate movement or pull-back of the catheter, each image corresponding to an echographic data set. The position of the catheter axis with respect to each echographic data set obtained during pull-back is recorded. The position, and optionally the velocity of the catheter tip are recorded. The recorded position of the catheter tip can be used to calculate a catheter pull-back trajectory in three-dimensional space. The images are stacked around the catheter pull-back trajectory by positioning the origin of a first image at a first recorded position, and positioning subsequent images at their respective distances from the first image, wherein each echographic data set is positioned so that the catheter axis is aligned with the catheter pull-back trajectory.

32 Claims, 4 Drawing Sheets

U.S. PATENT DOCUMENTS

| | | | |
|---|---|---|---|
| 5,315,512 | 5/1994 | Roth | 364/413.25 |
| 5,345,938 | 9/1994 | Nishiki et al. | 128/660.04 |
| 5,398,691 | 3/1995 | Martin et al. | 128/662.06 |
| 5,479,938 | 1/1996 | Weier | 128/772 |
| 5,515,853 | 5/1996 | Smith et al. | 128/661.01 |
| 5,546,949 | 8/1996 | Frazin et al. | 128/662.06 |

OTHER PUBLICATIONS

"Detection of Heart Atrial Septal Defect with the Aid of Ultrasonic Intravenous Probes", *Ultrasonics*, Kimoto et al., pp. 82–86 (Apr.–Jun. 1964).

"Intracardiac Scanning of the Heart with the aid of Ultrasonic Intravenous Probe", *Japanese Heart Journal*, Ryozo Omoto, Vol. 8, pp. 569–581 (Nov. 1967).

"Ultrasonic Guidance of Laser Atherectomy", *International Journal of Cardiac Imaging*, Aretz et al., vol. 6, pp. 231–237 (1991).

"Accurate Three–Dimensional Reconstruction of Intravascular Ultrasound Data, Spatially Correct Three–Dimensional Reconstructions", *Circulation*, Evans et al., Vol. 93 No. 3, pp. 567–576 Feb. 1, 1996).

Roelandt et al., Three–dimensional Reconstruction of Intracoronary Ultrasound Images, Circulation. 1994; 90:1044–1055.

ENHANCED ACCURACY OF THREE-DIMENSIONAL INTRALUMINAL ULTRASOUND (ILUS) IMAGE RECONSTRUCTION

FIELD OF THE INVENTION

This invention relates to methods and apparatus for ultrasound imaging within a body cavity or tureen, and more particularly relates to methods and apparatus which enhance the accuracy of three-dimensional (3D) image reconstruction where the 3D image is reconstructed from a series of images taken over a nonlinear path.

BACKGROUND OF THE INVENTION

Intravascular ultrasound imaging is now a common technique used to determine the position and characteristics of stenotic lesions in the arteries of a patient. Presently, 3D images of a region of a vessel are generated by acquiring image data from an ultrasound transducer during pull-back of the transducer within a region of interest, and then stacking the sequence of 2D images thus acquired to generate a 3D image. In procedures commonly used, the 2D images are stacked equidistantly along a straight centerline, assuming uniform velocity of pull-back. If pull-back velocity is nonuniform, then the position of each image is registered, and images are stacked at equidistant registered positions. Although non-uniform pull-back does not lead to 3D distortion, it may result in gaps in the image due to nonuniform spacing. These methods assume that the transducer follows a linear path during pull-back, whereas in reality the path is often curved in 3D space. Thus, by making this assumption, substantial error may be introduced into the 3D reconstruction, resulting in an image having significant distortion in the 3D representation of reality.

At least one attempt has recently been made to correct for this error by generating a 3D catheter centerline, and then stacking 2D images according to the geometry of the catheter centerline. See Slager et al., The Thorax Center Journal 7/3:36–37 (1995); Roelandt et al., Circulation 90(2):1044–1055 (1994); Slager et al., Journal of the American College of Cardiology, 25: 144A (1995); and Laban et al., Thorax Center, University Hospital, Rotterdam, Netherlands, "ANGUS: A new Approach to Three-dimensional Reconstruction of Coronary Vessels by Combined Use of Angiography and Intravascular Ultrasound"; these and all other references cited herein are expressly incorporated by reference as if fully set forth herein in their entirety. According to the Slager method, use is made of a catheter having radiopaque markers, and the catheter centerline is reconstructed from data obtained through bi-plane fluoroscopy before and/or during catheter pull-back. The use of fluoroscopy as a technique for the determination of a 3D centerline is, however, not without certain drawbacks and side effects. Thus, a need exists for apparatus and methods to determine pull-back trajectory without using fluoroscopy, so as to permit accurate 3D reconstruction from sequential ultrasound images.

SUMMARY OF THE INVENTION

We have discovered methods and apparatus for imaging an organ or internal structure within a body to obtain accurate 3D reconstruction of the organ or internal structure. The methods and apparatus will find applicability to the coronary arteries, arteries generally, and more generally the vascular system, as well as to imaging anatomic spaces within organs, such as the cavities of the heart, including the atria and ventricles.

The apparatus of the invention includes both an ultrasound imaging catheter system and a catheter tracking system. The ultrasound imaging system generally is provided in the form of a conventional intraluminal catheter having ultrasound imaging capabilities. For details on the general design and construction of such catheters, the reader is directed to Yock, U.S. Pat. Nos. 4,794,931, 5,000,185, and 5,313,949; Sieben et al., U.S. Pat. Nos. 5,243,988, and 5,353,798; Crowley et al., U.S. Pat. No. 4,951,677; Pomeranz, U.S. Pat. No. 5,095,911, Griffith et al., U.S. Pat. No. 4,841,977, Maroney et al., U.S. Pat. No. 5,373,849, Born et al., U.S. Pat. No. 5,176,141, Lancee et al., U.S. Pat. No. 5,240,003, Lancee et al., U.S. Pat. No. 5,375,602, Gardineer et at., U.S. Pat. No. 5,373,845, Seward et al., Mayo Clinic Proceedings 71(7):629–635 (1996), Packer et al., Cardiostim Conference 833 (1994), "Ultrasound Cardioscopy," Eur. J.C.P.E. 4(2):193 (June 1994), Eberle et al., U.S. Pat. No. 5,453,575, Eberle et al., U.S. Pat. No. 5,368,037, Eberle et at., U.S. Pat. No. 5,183,048, Eberle et al., U.S. Pat. No. 5,167,233, Eberle et at., U.S. Pat. No. 4,917,097, Eberle et at., U.S. Pat. No. 5,135,486, and other references well known in the art relating to intraluminal ultrasound devices and modalities. The catheter will typically have proximal and distal regions, and will include an imaging tip located in the distal region. Such catheters have an ability to obtain echographic images of the area surrounding the imaging tip when located in a region of interest inside the body of a patient. The catheter, and its associated electronic circuitry, will also be capable of defining the position of the catheter axis with respect to each echographic data set obtained in the region of interest.

The catheter tracking system generally includes at least one ultrasound transducer mounted adjacent the imaging tip of the catheter, the signal of which is used to track the location and/or angulation of the imaging tip during movement. In the reception mode, the signal used to track location of the imaging tip is electric, while in the emission mode the signal will be acoustic. The movement is usually pull-back, but also including lateral movement in all six degrees of freedom ((x,y,z) and three angles). In the remaining disclosure we shall typically discuss pull-back alone, but it will be understood that all other forms of movement are contemplated. In another embodiment, a pair of transducers mark the location of the imaging tip during pull-back. The pair of closely spaced transducers define a line which approximates the tangent to the curve defined by the catheter at that point. Thus, angulation of the catheter is determined by finding the line through the positions of at least two transducers adjacent the imaging tip as an approximation of the catheter tangent. Where only a single transducer marks the location of the catheter tip during pull-back, the catheter tangent is approximated by the line defined by two sequential positions of the marker transducer during pull-back.

The catheter tracking system further includes a number of transducers located away from the intraluminal ultrasound (ILUS) catheter, generally two or more, more preferably three or more, more preferably four or more. These transducers form a reference frame, and they may be located internally and/or externally of the patient. The tracking system further includes electronic circuitry for activating certain transducers to generate ultrasound signals for reception by certain other ultrasound transducers. The system also includes circuitry for measuring elapsed time between generation of the ultrasound signals and reception by respective other ultrasound transducers. Moreover, the tracking system will include electronic circuitry for calculating positions of the frame transducers and catheter tip transducers relative to each other using known velocity of ultrasound waves and triangulation, and using measured elapsed times. This tracking system allows the user to determine the 3D coordinates (x, y, z) of each marker transducer at successive times during catheter pull-back. An example of a catheter tracking system, and its method of use to determine 3D coordinates (x, y, z) of a moving point, are described in Smith et al., U.S. Pat. No. 5,515,853, the contents of which are incorporated herein by reference, and will not be further discussed here.

The methods of the invention will generally include a step of positioning the ILUS catheter imaging tip within the patient at a region of interest. The ILUS catheter may then be operated to obtain a series of echographic images during catheter pull-back. In a preferred embodiment, the pull-back is an ECG-gated pull-back as disclosed in Roelandt et at., Circulation 90(2): 1044–1055 (1994) and Laban et al., Thorax Center, University Hospital, Rotterdam, Netherlands, "ANGUS: A new Approach to Three-dimensional Reconstruction of Coronary Vessels by Combined Use of Angiography and Intravascular Ultrasound." During acquisition of each echographic data set, the position of the catheter axis with respect to the data set is determined and recorded. This step is done by imaging. Moreover, the 3D coordinates of the catheter tip are also determined and recorded for each echographic data set. This step is done by the tracking system. The recorded positions of the catheter tip are used to calculate a catheter pull-back trajectory in 3D space, taking into account a correction for the imaging transducer not being positioned at exactly the location of the one or more marker transducers. The echographic images are stacked around the catheter trajectory. This step is the 3D reconstruction. The origin of a first echographic data set is placed at the first recorded position, and then each subsequent image is positioned at its respective distance from the first image. During this positioning step, it is preferable to align the recorded catheter axis with the pull-back trajectory so that each image data set has the proper angle of orientation relative to the pull-back trajectory.

DETAILED DESCRIPTION

Figure 1:
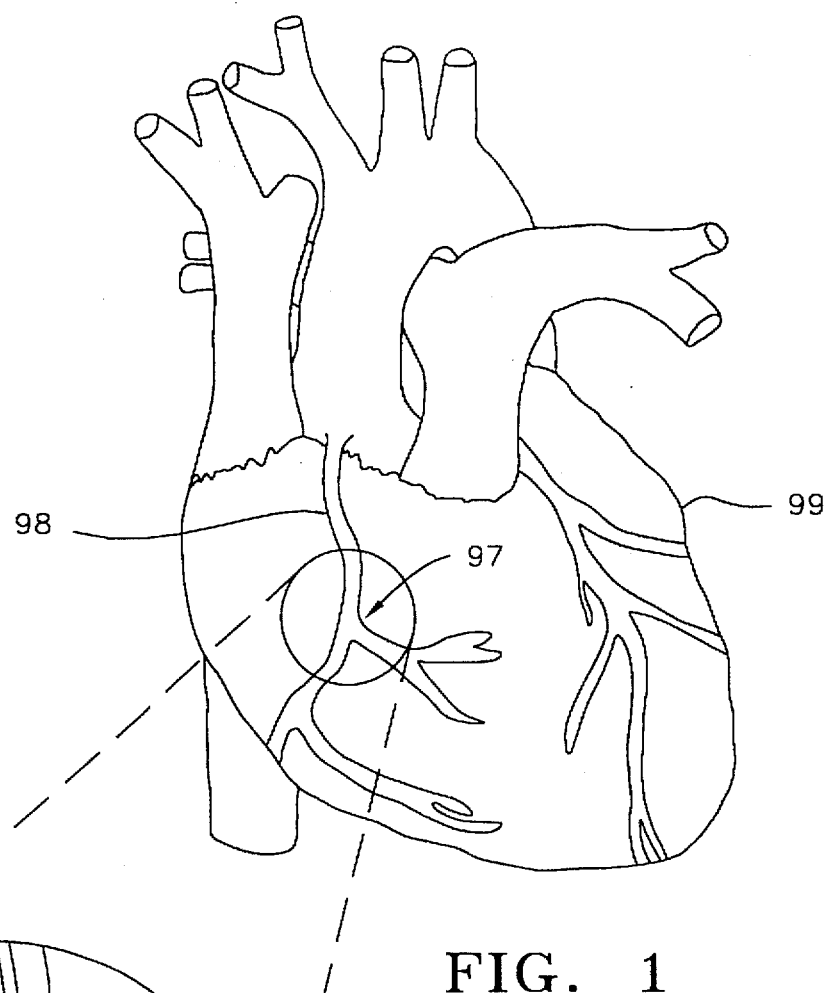
FIG. 1 depicts a human heart as a site for use of the method and apparatus disclosed herein.
Figure 2:
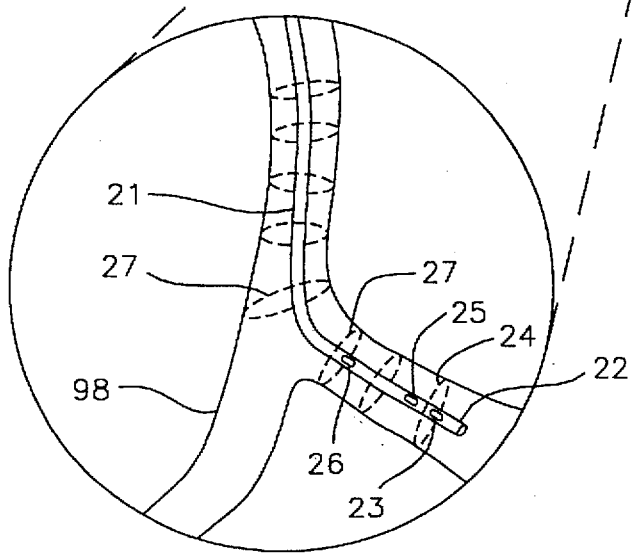
FIG. 2 depicts an exploded view of a region of the coronary arteries having an ILUS catheter positioned in a region of interest.

The methods disclosed herein are applicable to ultrasound imaging of the coronary arteries as depicted in FIG. 1, or to any body cavity where the image is to be obtained over a region potentially having a curvature. With reference to FIG. 1, heart 99 includes coronary arteries 98 which follow a tortuous path along the surface of the heart, having curvatures in many locations. FIG. 2 shows an exploded view of curvature 97, having an ILUS catheter disposed within a region of interest therein. Catheter 21 has distal end 22 and a proximal end (not shown), and is generally designed in accordance with imaging catheters known in the art. The catheter thus includes an intraluminal ultrasound imaging system capable of obtaining echographic images of the surrounding of catheter tip 22. The imaging system includes transducer 23 and its associated electronics for displaying an echographic data set, e.g., obtained by scanning transducer 23 over a 360-degree path 24 about distal tip 22 of catheter 21, or by a sector scan which makes a 60 or 90 degree scan. In an alternative embodiment, transducer 23 is replaced by a phased array as disclosed in Griffith et al., U.S. Pat. No. 4,841,977. Scanning of the vessel interior is repeated many times during pull-back to obtain a plurality of echographic data sets taken at a sequence of positions 27 within vessel 98.

In one embodiment, each echographic data set obtained during pull-back comprises a transverse or cross-sectional image of the vessel at the point of the image, as shown in FIG. 2. In another embodiment, each image represents essentially a conical plane having its top at the position of the imaging transducer. In this case, the top angle of the conical plane is usually large, and typically 150–170 degrees. In another embodiment, each echographic data set represents essentially a 3D cloud having its origin at the position of the ultrasound imaging transducer.

The apparatus herein further includes a catheter tracking system which enables real-time determination of the 3D coordinates and angulation of the catheter imaging tip during use within a body. The tracking system includes at least one transducer 25 mounted on the catheter and typically adjacent the imaging tip 23, as shown in FIG. 2. Transducer 25 can be mounted either proximal or distal to scanning transducer 23. However, a distal mount may lead to image artifacts because of transducer leads which cross the image plane. In another embodiment, catheter 21 includes two tracking transducers 25 and 26 spaced by a short distance. Tracking system resolution is the limiting factor in determining how close the two transducers can be placed. It is desired to have the two transducers placed as close as possible. Because resolution permits determination of position to within about 1 mm, it is best to space the tracking transducers by greater than 5 mm, more preferably greater than 7 mm, more preferably greater than 9 mm, and most preferably at or greater than about 10 mm, in order to minimize the percent error due to the limits on resolution. In any case, it is best to limit the spacing of the tracking transducers to no greater than about 15 mm or less, more preferably no greater than about 12 mm or less, more preferably no greater than about 10 mm or less, with about a 10 mm spacing being most preferred.

It is desirable to be able to calculate the tangent to the catheter centerline or to the trajectory of the imaging transducer at each point where echographic data is acquired. In one embodiment, where two or more tracking transducers are employed, the tangent is approximated by the line defined by the two or more points determined by the location of the tracking transducers. In another embodiment, where only one tracking transducer is employed, the tangent is approximated by the line through two points determined by the successive locations of the tracking transducer at two positions during pull-back. The tangent, or angulation, once determined, provides the proper angle of placement of each echographic data set since each data set may be placed so that the recorded catheter axis for each data set coincides with the tangent at the point where the echographic data set was recorded. Numerous averaging techniques known in the art can be used to smooth large deviations in the obtained trajectory caused by stochastic errors or resolution deficiency.

The catheter tracking system also includes a number of transducers located away from the ILUS catheter which collectively define a reference frame. It is desired to have at least three transducers away from the catheter and in the reference frame so that the tracking transducer and the reference frame transducers are not all included in one plane. The design and use of a catheter tracking system is fully discussed in Smith et at., U.S. Pat. No. 5,515,853.

In use, the ILUS catheter is deployed according to procedures well known in the art. For imaging in the coronary artery, the catheter is inserted through an incision in the femoral artery and is advanced upwardly through the descending aorta, typically with assistance from a guiding catheter, until it crosses the aortic arch and reaches the coronary arteries. Where the region of interest lies within a different vessel or organ, the means for entry will obviously differ, but will follow established techniques known in the art. The ILUS catheter is positioned so that the imaging tip lies within a region of interest inside the body of a patient, as depicted in FIG. 2. The catheter imaging system is then carried through a pull-back sequence, optionally using an automated pull-back device as disclosed by Webler et at., U.S. Pat. Nos. 5,361,768 and 5,485,846. During pull-back, a series of echographic data sets is obtained, each of which will provide the necessary input to produce an image which can be displayed according to processes and using electronic equipment well known in the art.

At the time each image is captured, the position of the catheter axis with respect to each echographic data set obtained during pull-back is known. During pull-back of the catheter imaging tip, it is also desired to record the position (x, y, z) and the time at each interval for which data is recorded, according to the method of U.S. Pat. No. 5,515, 853. From this information, it is possible to calculate the velocity of catheter tip movement and to record this information as well. Moreover, it is desired to determine and record the angulation of the imaging tip for each image using the coordinates (x, y, z) of the one or more tracking transducers as discussed above.

The coordinates (x, y, z) of each point of image acquisition along the catheter pull-back path are then used in conjunction with the time data to reconstruct a 3D image by stacking the echographic images around the catheter pull-back trajectory. The origin of the first image is placed at a first recorded position. The next image is then positioned at its respective distance from the first image, and this process is repeated until all images within the region of interest have been placed along the pull-back trajectory. Each echographic data set is adjusted so that the catheter axis recorded for that data set is aligned with the catheter pull-back trajectory. In this manner, for cross-sectional scanning, each echographic data set is oriented at a substantially 90-degree angle to the longitudinal axis of the ILUS catheter. Linear interpolation is performed between digitized adjacent image sets, resulting in a volumetric (voxel) data set, as described in Evans et al., Circulation 93:567–576 (1996), incorporated herein by reference. The voxel data set can be resliced, creating a new series of 2D flames. 3D images can be created by processing the data with algorithms developed specifically for voxel-based image display (Sonoview, Pura Labs). The resulting images are displayed on a workstation for display and analysis.

Where the echographic data sets are 3D clouds, each cloud may overlap at its boundaries with the adjacent image cloud. Thus, it may be desired to make certain adjustments in the echographic data to eliminate distortions which may occur at the boundaries between overlapping images.

Moreover, error may occur due to what is known as "sock rotation," which refers to the rotational orientation of each echographic data set relative to a fixed reference. We adjust for this error by using anatomic landmarks within the vessel or cavity being imaged, so that the rotational orientation of each data set is adjusted relative to the placement of that landmark.

Adjustment may also be made for image rotation caused by twist of the catheter during pull-back due to bends in different planes. This typically shows up as image rotation which may distort a reconstructed image if not corrected for. This distortion arises because the images are rotated to a different degree around their origin along their path during pull-back. This phenomenon, and a solution to correct for it, is described in Laban et al., Thorax Center, University Hospital, Rotterdam, Netherlands, "ANGUS: A new Approach to Three-dimensional Reconstruction of Coronary Vessels by Combined Use of Angiography and Intravascular Ultrasound," and will not be further discussed here in the interest of brevity.

In another embodiment, the catheter tip position is recorded during pull-back by using a magnetic position and orientation determining system as described by Acker et al., International Application No. PCT/US94/11298 (U.S. Ser. No. 8/132,479, filed Oct. 6, 1993), and Ben-Haim et al., International Application No. PCT/US95/01103 (U.S. Ser. No. 08/293,859, filed Apr. 19, 1994), incorporated herein by reference.

In another embodiment, the catheter tip position is recorded during pull-back by using an electromagnetic position and orientation determining system as described by Aretz et al., International Journal of Cardiac Imaging 6:231–237 (1991), incorporated herein by reference.

EXAMPLE 1

3D Reconstruction Using Catheter with One Omni-Directional Tracking Transducer

Figure 3:
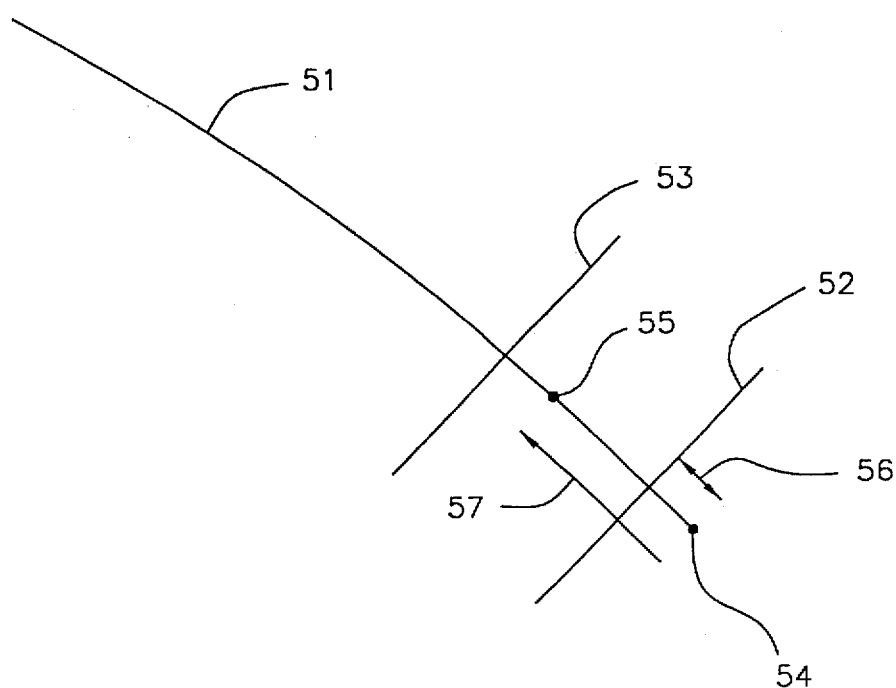
FIG. 3 depicts a pull-back of an ILUS catheter having one omni-directional tracking transducer.

Stacking of images to obtain 3D reconstruction is accomplished using a catheter with one tracking transducer by calculating an approximate tangent to the pull-back trajectory using two successive points for the tracking transducer, as depicted in FIG. 3. Transverse images 52 and 53 are obtained during pull-back 57 along trajectory 51. At a first point in time, $t=t_1$, the tracking transducer lies at position 1, corresponding to point 54. The image plane 52 is displaced by distance 56 (s) from position 1, and this displacement s corresponds to the distance between a distal tracking transducer and a slightly proximal scanning transducer. At a second point in time, $t=t_2$, the tracking transducer lies at position 2, corresponding to point 55. The image plane 53 is again displaced by distance s from position 2.

Thus, at position 1 ($t=t_1$), the tip coordinates are given by ($x_1$, $y_1$, $z_1$), while at position 2 ($t=t_2$), the tip coordinates are given by ($x_2$, $y_2$, $z_2$). The direction and the length of the vector between position 1 and position 2 is given by the vector $$(x_2-x_1, y_2-y_1, z_2-z_1)$$

The direction and the length of the vector between position 1 and the image plane 52 is given by the vector $$\frac{s}{\sqrt{(x_2-x_1)^2+(y_2-y_1)^2+(z_2-z_1)^2}} (x_2-x_1, y_2-y_1, z_2-z_1)$$

The normal vector on image plane 52 is $$(n_1, n_2, n_3) = \frac{(x_2-x_1, y_2-y_1, z_2-z_1)}{\sqrt{(x_2-x_1)^2+(y_2-y_1)^2+(z_2-z_1)^2}}$$

This vector positions image plane 52 at a 90° angle to the tangent, the direction of which is approximated by the direction of the vector between position 1 and position 2. The mathematical description of image plan 52 is therefore defined by $$n_1x + n_2y + n_3z = n_1\left(x_1 + \frac{s(x_2-x_1)}{\sqrt{(x_2-x_1)^2+(y_2-y_1)^2+(z_2-z_1)^2}}\right) +$$

$$n_2\left(y_1 + \frac{s(y_2-y_1)}{\sqrt{(x_2-x_1)^2+(y_2-y_1)^2+(z_2-z_1)^2}}\right) +$$

$$n_3\left(z_1 + \frac{s(z_2-z_1)}{\sqrt{(x_2-x_1)^2+(y_2-y_1)^2+(z_2-z_1)^2}}\right)$$

Therefore, in reconstruction, the coordinates of the origin are given by $$\left(x_1 + \frac{s(x_2-x_1)}{\sqrt{(x_2-x_1)^2+(y_2-y_1)^2+(z_2-z_1)^2}}\right),$$

$$\left(y_1 + \frac{s(y_2-y_1)}{\sqrt{(x_2-x_1)^2+(y_2-y_1)^2+(z_2-z_1)^2}}\right),$$

$$\left(z_1 + \frac{s(z_2-z_1)}{\sqrt{(x_2-x_1)^2+(y_2-y_1)^2+(z_2-z_1)^2}}\right)$$

and the angulation of the plane is defined by its normal vector ($n_1$, $n_2$, $n_3$). Image plane 53 is defined analogously after definition of a position 3, by substitution 1→2 and 2→3 in ($x_1$, $y_1$, $z_1$) and ($x_2$, $Y_2$, $Z_2$).

Figure 4:
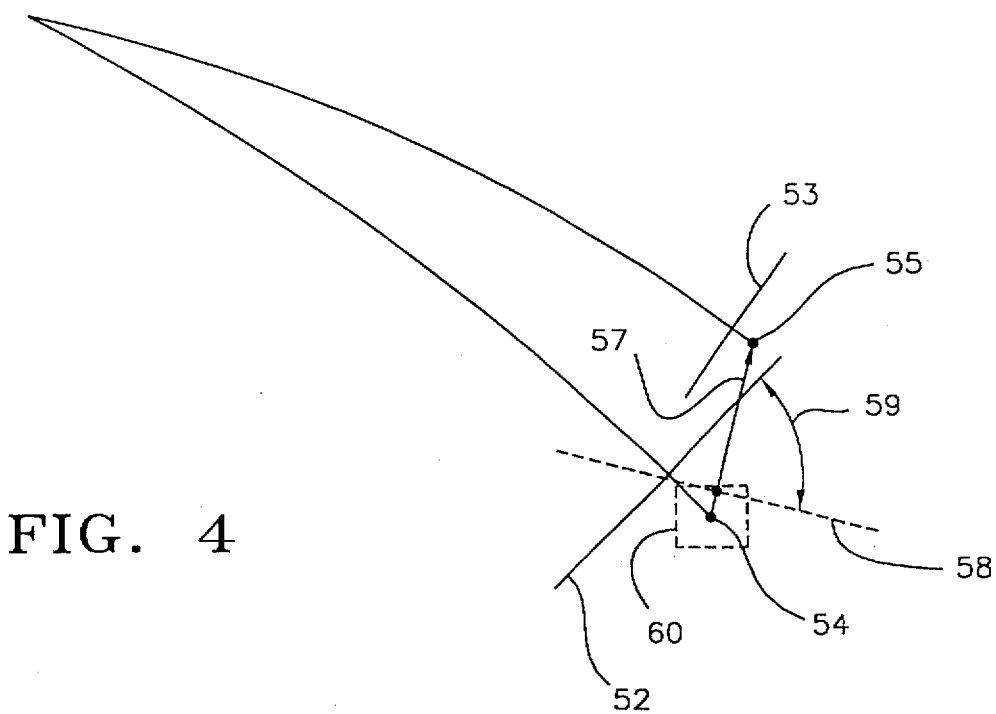
FIG. 4 depicts lateral movement which may occur during pull-back of the ILUS catheter shown in FIG. 3.

It will be understood that this system and method of calculation has a potential for significant error if the pull-back is not done in line with the catheter axis at the catheter tip location. This error is therefore likely to occur where there is substantial lateral movement during pull-back, such as would occur in an anatomic cavity within an organ (e.g., the chambers of the heart). This error is illustrated in FIG. 4 where it can be seen that, for a pull-back starting at position 54, the entire trajectory is displaced by lateral movement 57. Thus, while the real image plane should be calculated as shown by plane 52, an assumed image plane 58 is generated instead, resulting in a substantial angulation error 59 between the real and assumed image planes. Moreover, this angulation error causes error 60 to occur in positioning the origin of the image.

EXAMPLE 2

3D Reconstruction Using Catheter With Two Omni-Directional Tracking Transducers

Figure 5:
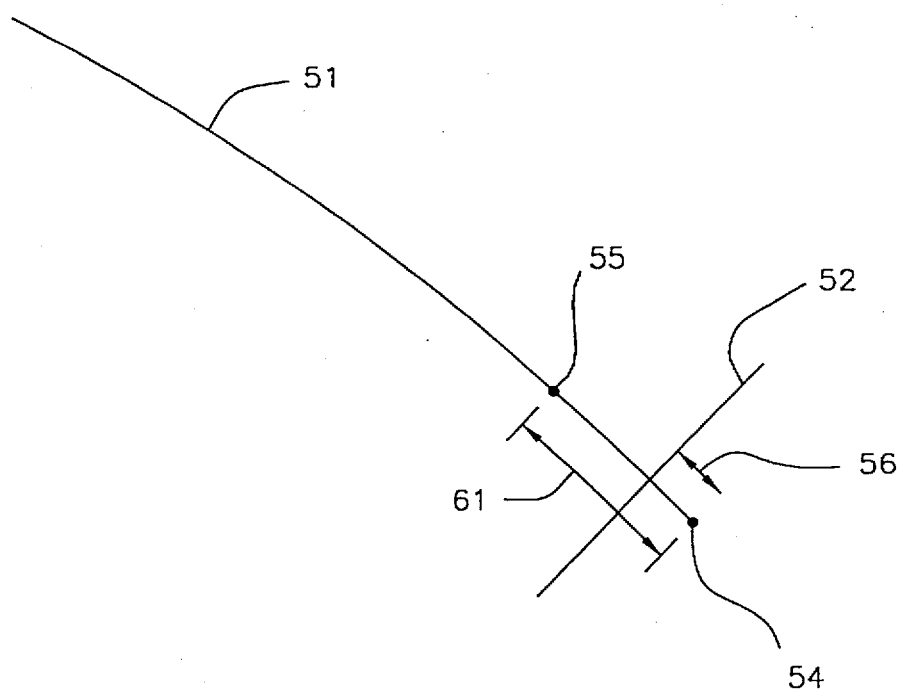
FIG. 5 depicts a pull-back of an ILUS catheter having two omni-directional tracking transducers.

Stacking of images to obtain 3D reconstruction is accomplished using a catheter with two tracking traducers by calculating an approximate tangent to the pull-back trajectory using the line between the two tracking transducers at the point in time when echographic image acquisition occurs, as depicted in FIG. 5. Transverse image 52 is obtained at time $t=t_1$ during pull-back along trajectory 51. At $t=t_1$, the first tracking transducer (transducer 1) lies at point 54 (position 1) while the second tracking transducer (transducer 2) lies at point 55 (position 2), separated by distance 1 corresponding to gap 61. Image plane 52 is displaced by distance 56 (s) from position 1, as described in Example 1.

Thus, at $t_1$, the tip coordinates for transducer 1 are given by ($x_1$, $y_1$, $z_1$), while the tip coordinates for transducer 2 are given by ($x_2$, $y_2$, $z_2$). The distance between transducers 1 and 2 is known and measured to be $$l = \sqrt{(x_2-x_1)^2+(y_2-y_1)^2+(z_2-z_1)^2}$$

and the image plane is positioned at distance s from transducer 1.

The normal vector on image plane 52 is $$(n_1, n_2, n_3) = \frac{(x_2-x_1, y_2-y_1, z_2-z_1)}{\sqrt{(x_2-x_1)^2+(y_2-y_1)^2+(z_2-z_1)^2}}$$

This vector positions image plane 52 at a substantially 90° angle to the tangent, the direction of which is approximated by the direction of the vector between transducers 1 and 2.

The mathematical description of image plane 52 is therefore defined by $$n_1x + n_2y + n_3z = n_1\left(x_1 + \frac{s(x_2-x_1)}{\sqrt{(x_2-x_1)^2+(y_2-y_1)^2+(z_2-z_1)^2}}\right) +$$

$$n_2\left(y_1 + \frac{s(y_2-y_1)}{\sqrt{(x_2-x_1)^2+(y_2-y_1)^2+(z_2-z_1)^2}}\right) +$$

$$n_3\left(z_1 + \frac{s(z_2-z_1)}{\sqrt{(x_2-x_1)^2+(y_2-y_1)^2+(z_2-z_1)^2}}\right)$$

Therefore, in reconstruction, the coordinates of the origin are given by $$\left(x_1 + \frac{s(x_2-x_1)}{\sqrt{(x_2-x_1)^2+(y_2-y_1)^2+(z_2-z_1)^2}}\right),$$

$$\left(y_1 + \frac{s(y_2-y_1)}{\sqrt{(x_2-x_1)^2+(y_2-y_1)^2+(z_2-z_1)^2}}\right),$$

$$\left(z_1 + \frac{s(z_2-z_1)}{\sqrt{(x_2-x_1)^2+(y_2-y_1)^2+(z_2-z_1)^2}}\right)$$

and the angulation of the plane is defined by its normal vector ($n_1$, $n_2$, $n_3$). During pull-back, this determination is repeated at $t=t_2(=t_1+\Delta t)$, at $t=t_3(=t_2+\Delta t)$, etc.

Figure 6A:
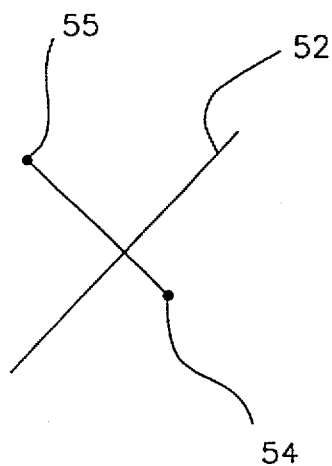
FIG. 6A depicts the ILUS catheter of FIG. 5 positioned within a linear region of a vessel.
Figure 6B:
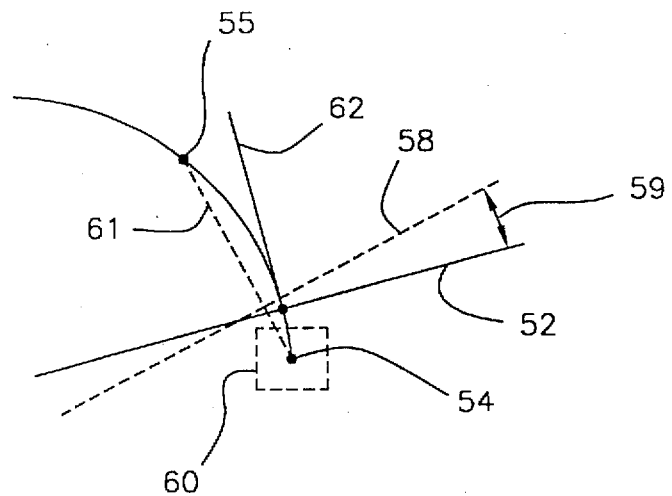
FIG. 6B depicts the ILUS catheter of FIG. 5 positioned within a highly curved region of a vessel.

It will be understood that this technique assumes that transducers 1 and 2 lie on a straight line with image plane 52 oriented perpendicularly, as shown in FIG. 6A. This assumption may lead to significant error where the catheter has a high degree of curvature between transducers 1 and 2 at any point of echographic data acquisition. This error is illustrated in FIG. 6B where it can be seen that, for an image acquired at $t_1$, the tangent is approximated by line 61, while the true tangent 62 has a significant displacement therefrom. Thus, while the real image plane should be calculated as shown by plane 52, an assumed image plane 58 is generated instead, resulting in angulation error 59 between the real and assumed image planes. Moreover, this angulation error causes error 60 to occur in positioning the origin of the image.

Although the foregoing invention has, for purposes of clarity of understanding, been described in some detail by way of illustration and example, it will be obvious that certain changes and modifications may be practiced which will still fall within the scope of the appended claims.

What is claimed is:

1. A method for imaging an organ or internal structure within a body to obtain three-dimensional reconstruction a region of interest of the organ or internal structure, said method comprising the steps of:

providing an intraluminal ultrasound imaging system capable of obtaining echographic images of the surrounding of a catheter imaging tip located inside the body of a patient;

providing a catheter tracking system comprising at least one ultrasound transducer mounted adjacent the imaging tip of an intraluminal ultrasound catheter for insertion into a patient, and a plurality of transducers located away from said intraluminal ultrasound catheter so as to form a reference frame with respect to the intraluminal ultrasound catheter tip;

positioning the intraluminal ultrasound catheter imaging tip within the region of interest within the organ or internal structure, obtaining a plurality of echographic images during movement of the catheter using the intraluminal ultrasound imaging system, each image corresponding to an echographic data set;

recording the positions of the catheter axis with respect to each echographic data set obtained during movement;

recording the position of the catheter tip during movement using the catheter tracking system; and stacking the images around a three-dimensional curved catheter movement trajectory by positioning the origin of a first image at a first recorded position, and positioning subsequent images at their respective distances from the first image and perpendicular to the catheter axis at the recorded positions along the curve.

2. The method of claim 1, wherein the catheter tracking system further comprises circuitry for (i) sequentially enabling respective ones of said ultrasound transducers to generate ultrasound signals for reception by respective other ones of said ultrasound transducers, (ii) sequentially measuring elapsed time between generation of said ultrasound signals and reception thereof by said respective other ones of said ultrasound transducers, and (iii) calculating via knowledge of velocity of ultrasonic waves and measured elapsed times, positions of the plurality of frame transducers relative to each other and positions of said catheter tip transducers relative to said plurality of frame transducers.

3. The method of claim 2, wherein the movement of the catheter is a pull-back.

4. The method of claim 3, wherein each echographic data set is positioned so that the recorded catheter axis position is aligned with an approximate tangent to the catheter pull-back trajectory.

5. The method of claim 4, wherein each echographic data set represents essentially a cross-sectional plane substantially perpendicular to the catheter axis at the catheter tip.

6. The method of claim 5, further comprising the step of repeating said sequence of generation and reception of ultrasound signals and calculation of transducer positions in order to determine displacement of said transducers and to determine their velocity.

7. The method of claim 5, further comprising the step of determining the catheter tip angulation.

8. The method of claim 7, wherein the catheter tracking system comprises at least two ultrasound transducers mounted adjacent the imaging tip, and the angulation is determined by finding the line through the positions of the at least two ultrasound transducers adjacent to the imaging tip of said intraluminal ultrasound catheter as an approximation of the catheter tip tangent.

9. The method of claim 7, wherein the angulation is determined by finding the line through two sequential positions of one of said ultrasound transducers.

10. The method of claim 5, wherein the at least one ultrasound transducer mounted adjacent the imaging catheter tip is omni-directional.

11. The method of claim 5, wherein the transducers located away from the intraluminal ultrasound catheter are omni-directional.

12. The method of claim 5, wherein the transducers located away from the intraluminal ultrasound catheter are located internally of the patient.

13. The method of claim 5, wherein the transducers located away from the intraluminal ultrasound catheter are located externally of the patient.

14. The method of claim 4, wherein each echographic data set represents a conical plane having its top at the position of the ultrasound imaging . transducer and a large top angle.

15. The method of claim 14, further comprising the step of repeating said sequence of generation and reception of ultrasound signals and calculation of transducer positions in order to determine displacement of said transducers and to determine their velocity.

16. The method of claim 14, further comprising the step of determining the catheter tip angulation.

17. The method of claim 16, wherein the catheter tracking system comprises at least two ultrasound transducers mounted adjacent the imaging tip, and the angulation is determined by finding the line through the positions of the at least two ultrasound transducers adjacent to the imaging tip of said intraluminal ultrasound catheter as an approximation of the catheter tip tangent.

18. The method of claim 16, wherein the angulation is determined by finding the line through two sequential positions of one of said ultrasound transducers.

19. The method of claim 14, wherein the at least one ultrasound transducers mounted adjacent the imaging catheter tip is omni-directional.

20. The method of claim 14, wherein the ultrasound transducers located away from the intraluminal ultrasound catheter are omni-directional.

21. The method of claim 14, wherein the transducers located away from the intraluminal ultrasound catheter are located internally of the patient.

22. The method of claim 14, wherein the transducers located away from the intraluminal ultrasound catheter are located externally of the patient.

23. The method of claim 14, wherein the top angle of the conical plane is 150–170 degrees.

24. The method of claim 4, wherein each echographic data set represents a three-dimensional cloud having its origin at the catheter imaging tip.

25. The method of claim 24, further comprising the step of repeating said sequence of generation and reception of ultrasound signals and calculation of transducer positions in order to determine displacement of said transducers and to determine their velocity.

26. The method of claim 24, further comprising the step of determining catheter tip angulation.

27. The method of claim 26, wherein the catheter tracking system comprises at least two ultrasound transducers mounted adjacent the imaging tip, and the angulation is determined by finding the line through the positions of the at least two ultrasound transducer adjacent to the imaging tip of said intraluminal ultrasound catheter as an approximation of the catheter tip tangent.

28. The method of claim 26, wherein the angulation is determined by finding the line through two sequential positions of one of said ultrasound transducers.

29. The method of claim 24, wherein the at least one transducer mounted adjacent the imaging tip is omni-directional.

30. The method of claim 24, wherein the transducers located away from the intra-luminal ultrasound catheter are omni-directional.

31. The method of claim 24, wherein the transducers located away from the intraluminal ultrasound catheter are located internally of the patient.

32. The method of claim 24, wherein the transducers located away from the intraluminal ultrasound catheter are located externally of the patient.

* * * * *